(12) United States Patent
Mora et al.

(10) Patent No.: US 11,033,645 B1
(45) Date of Patent: Jun. 15, 2021

(54) APPARATUS FOR RAPID DISINFECTION OF PERSONAL ITEMS

(71) Applicant: 1Lss, Inc, Los Angeles, CA (US)

(72) Inventors: Fernando Mora, Reseda, CA (US); Alejandro Baca, North Hollywood, CA (US); Mydul R. Islam, Los Angeles, CA (US)

(73) Assignee: 1LSS, INC, Los Angeles, CA (US)

( * ) Notice: Subject to any disclaimer, the term of this patent is extended or adjusted under 35 U.S.C. 154(b) by 0 days.

(21) Appl. No.: 16/899,135

(22) Filed: Jun. 11, 2020

(51) Int. Cl.
*A61L 2/10* (2006.01)
*A61L 2/24* (2006.01)
*A61L 2/26* (2006.01)

(52) U.S. Cl.
CPC .................. *A61L 2/10* (2013.01); *A61L 2/24* (2013.01); *A61L 2/26* (2013.01); *A61L 2202/11* (2013.01); *A61L 2202/14* (2013.01)

(58) Field of Classification Search
CPC .................. A61L 2/20; A61L 2/24
See application file for complete search history.

(56) References Cited

U.S. PATENT DOCUMENTS

| | | | | |
|---|---|---|---|---|
| 4,877,964 A * | 10/1989 | Tanaka | ...................... | A61L 2/10 250/455.11 |
| 5,439,642 A * | 8/1995 | Hagmann | .................. | A61L 2/08 422/22 |
| 8,964,405 B2 | 2/2015 | La Porte et al. | | |
| 9,339,576 B2 | 5/2016 | LaPorte et al. | | |
| 2008/0199353 A1 * | 8/2008 | Mlodzinski | ............. | G07F 11/48 422/24 |
| 2010/0044582 A1 | 2/2010 | Cooper et al. | | |
| 2013/0277574 A1 * | 10/2013 | Dayton | ..................... | A61L 2/10 250/455.11 |
| 2017/0202988 A1 * | 7/2017 | Clark | ........................ | A61L 2/26 |
| 2017/0304472 A1 * | 10/2017 | Neister | ................ | A61N 5/0624 |
| 2018/0258579 A1 * | 9/2018 | Kim | ........................ | A47B 55/00 |

OTHER PUBLICATIONS

Alex Warner, Casetify Launched a Portable UV Sanitizer That Kills 99.9% of Germs on Your Phone, People Jun. 10, 2020.
Casetify webpage offering product available at least as early as Jun. 10, 2020.

* cited by examiner

*Primary Examiner* — Kevin Joyner
(74) *Attorney, Agent, or Firm* — Thomas Coester Intellectual Property

(57) ABSTRACT

Disinfectors that are touchless, high speed, or both for personal electronic devices and the like. A housing defines an internal volume including a disinfection zone and an object entry port of a size to permit entry by an object of interest with exposed surface area. At least one emitter projects a stripe of UV-C light into the disinfection zone. A drive under the control or a controller transport causes relative movement between the object and the emitter to expose the surface area to greater than 3 $mJ/cm^2$ of UV-C light in less than 90 seconds.

19 Claims, 10 Drawing Sheets

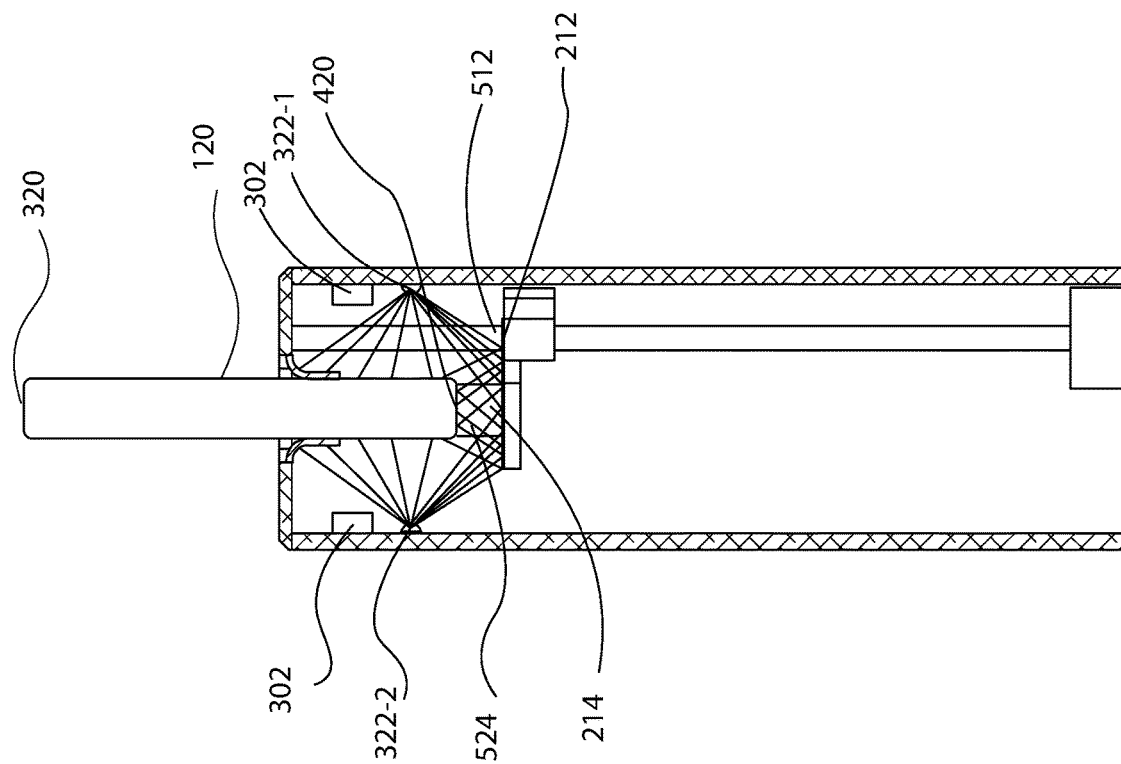
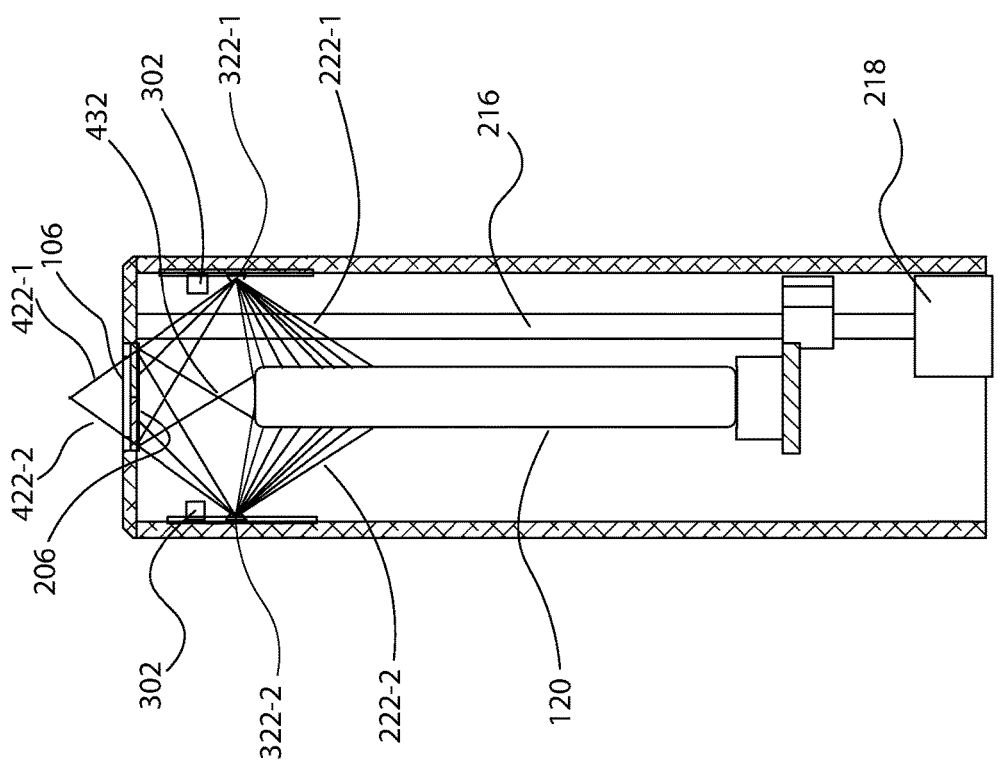

APPARATUS FOR RAPID DISINFECTION OF PERSONAL ITEMS

BACKGROUND

Technological Field

Embodiments of the invention relate ultraviolet disinfection. More specifically embodiments of the invention relate to rapid ultraviolet disinfection of personal items.

Background

The novel corona virus that causes COVID-19 has been highly disruptive to the global economy. It has also highlighted the degree to which contagion can be spread through contact with everyday items. Personal electronic devices such as cell phones have been found to be significant vectors for viral and bacterial transmission. Taking the smart phones as an example, the normal use of the touch screen result in repeated hand contact with the screen. That contact can result in pathogens transferred from the user's hands to the screen. The pathogens may originate on any surface that the user touches, such as a grocery cart, handrail in public transportation, doorknob are just some examples. When a call comes in, the user then often puts the phone to their ear and risks transfer of the pathogens to their face including potential exposure to the mucous membranes in the mouth and nose which are often the pathway to infection.

In an effort to combat the spread of the novel corona virus, particular attention in being given to hand washing. Unfortunately, immediately after handwashing the hands are often again contaminated through contact with a pathogenic rich smart phone or other such item. While some devices exist to disinfect smartphones, the typical model is a clam shell enclosure that requires the phone reside therein for thirty minutes or more to complete the disinfecting process. Such time requirement significantly reduces the utility of the device. Moreover, a user is required to manipulate the clam shell to open and close it, providing additional opportunities for transfer of pathogens.

BRIEF DESCRIPTION OF THE DRAWINGS

Embodiments of the invention are illustrated by way of example and not by way of limitation in the figures of the accompanying drawings in which like references indicate similar elements. It should be noted that different references to "an" or "one" embodiment in this disclosure are not necessarily to the same embodiment, and such references mean at least one.

FIGS. 4A-4C illustrate edge disinfection schematically according to one embodiment of the invention.

DETAILED DESCRIPTION

Embodiments of the invention provide a high-speed hands-free apparatus to destroy pathogens on personal items. By bringing the time to complete the disinfection process into a range consistent with the time required for proper handwashing, wider community adoption and reduced community infection is expected. Furthermore, event without the reduced time benefit a touchless design reduces the risk of disease transmission.

Figure 1:
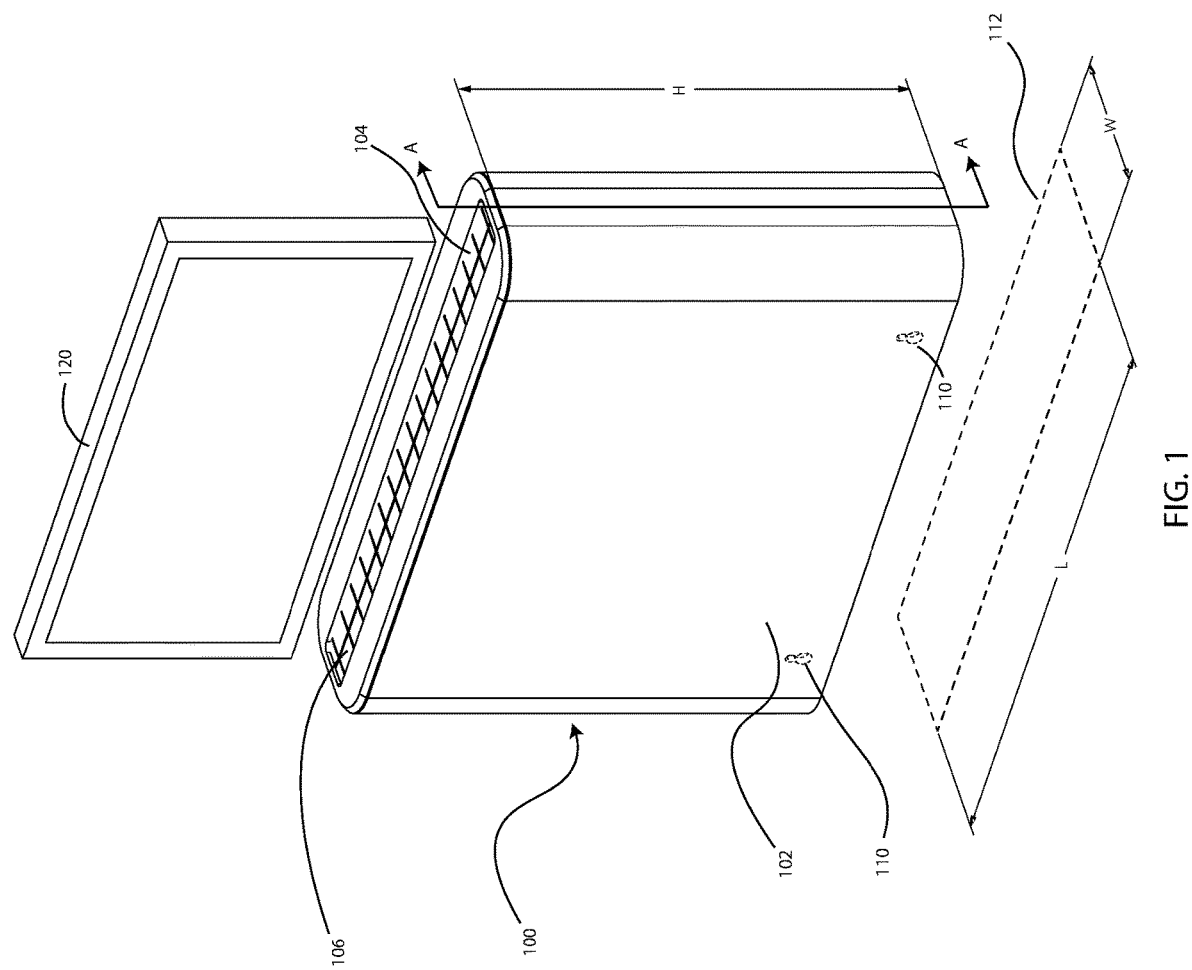
FIG. 1 is a perspective view of a disinfecting unit and target object according to one embodiment of the invention.

FIG. 1 is a perspective view of a disinfecting unit and target object according to one embodiment of the invention. Disinfector 100 has a housing 102 with an internal volume and particularly a disinfection zone sized to accept an object of interest 120 for disinfection. For example, in some embodiments the objects of interest 120 are smart phones and the disinfection zone is sized to accommodate the desired range of smart phone sizes. Other embodiment may be sized to accept a range of personal items such as personal electronic devices (PEDs), credit cards, wallets and the like. PEDs include smart phones, but may also include tablets, phablets, pagers, personal digital assistants, e-readers and the like. Ultraviolet (UV) light of an effective wavelength and intensity is applied within the disinfection zone to destroy pathogens on the object of interest 120. In one embodiment, the selected wavelength of light is 200 nm to 280 nm. In some embodiments, the wavelength is in the range of 240 nm and 280 nm. As used herein, "disinfection zone" refers to the volume within the housing 102 in which disinfection occurs.

Housing 102 defines an object access port 104. Object access port 104 is in communication with the interior volume and size to accept and object of interest 120. One embodiment is sized to accept most smart phones. Currently, the larger end of the smart phone size range is at about 8.5 cm×16 cm×1.2 cm. If the embodiment is designed to accept the phone in landscape orientation, the port 104 may be in the range or 16.2-16.5 cm×1.3-1.5 cm to accommodate such a phone in a case. If the embodiment is designed to accept the phone in portrait orientation, the port 104 may be in the range or 8.7-9.00 cm×1.3-1.5 cm to accommodate such a phone in a case. These are merely examples and other dimension may be selected in different embodiments of the invention. It should be understood that the housing ratio of height to length is driven, at least in part, by which orientation the object of interest is to be accepted. By accepting the phone in a landscape orientation, the range of movement (as described below) is reduced. In one embodiment, the housing, in use, has a generally vertical orientation and the object access port is in an upper surface of the housing. This configuration allows gravity to help the object of interest remain in a desired orientation as discussed in more detail below. Other embodiments may have the object access port 104 in another surface of the housing 102.

The access port 104 is occluded by resilient fingers 106. Resilient fingers 106 occlude the access port to prevent the escape of UV light from within the housing 102 and support the object of interest 120 as it enters the housing. In some embodiments, an underside of the resilient fingers 106 is reflective. Generally, resilient fingers 106 could be formed of silicone or another generally nonreactive elastomer. The undersurface can be treated with a reflective coating. In some embodiments, monolithic resilient wipers may be used instead of the resilient fingers 106, but this may not be as effective for blocking the light when different sized objects 120 are used with the same device.

In some embodiments, housing 102 has a gross geometry that does not change during use. As used herein, "gross geometry" refers to the bounding volume required to contain the housing. In the shown embodiment, a rectangular box with a length, width, and height can bound housing 102. None of these bounding dimensions change during use. In contra distinction devices, such as clam shell devices that hinge open necessarily require a different bounding volume when open versus when closed and have different gross geometries in the different orientations.

Some embodiments have a small footprint. As use herein footprint is defined as the area given by length times width of the minimum bounding box that can enclose the disinfector at its widest point in the plane normal to the height dimension. That is, overhanging parts and extending arms for example are deemed to impact the "footprint." The shown embodiment, disinfector 100 has a substantially uniform cross section for its full height. The footprint 112 has an area of L×W as shown in FIG. 1. In one embodiment, the disinfector 100 has length, width and height of 180 mm, 50 mm and 135 mm respectively. This yields a footprint of 9000 mm$^2$ and a gross geometry that fits in a bounding box that is 180 mm×50 mm×135 mm.

Figure 1A:
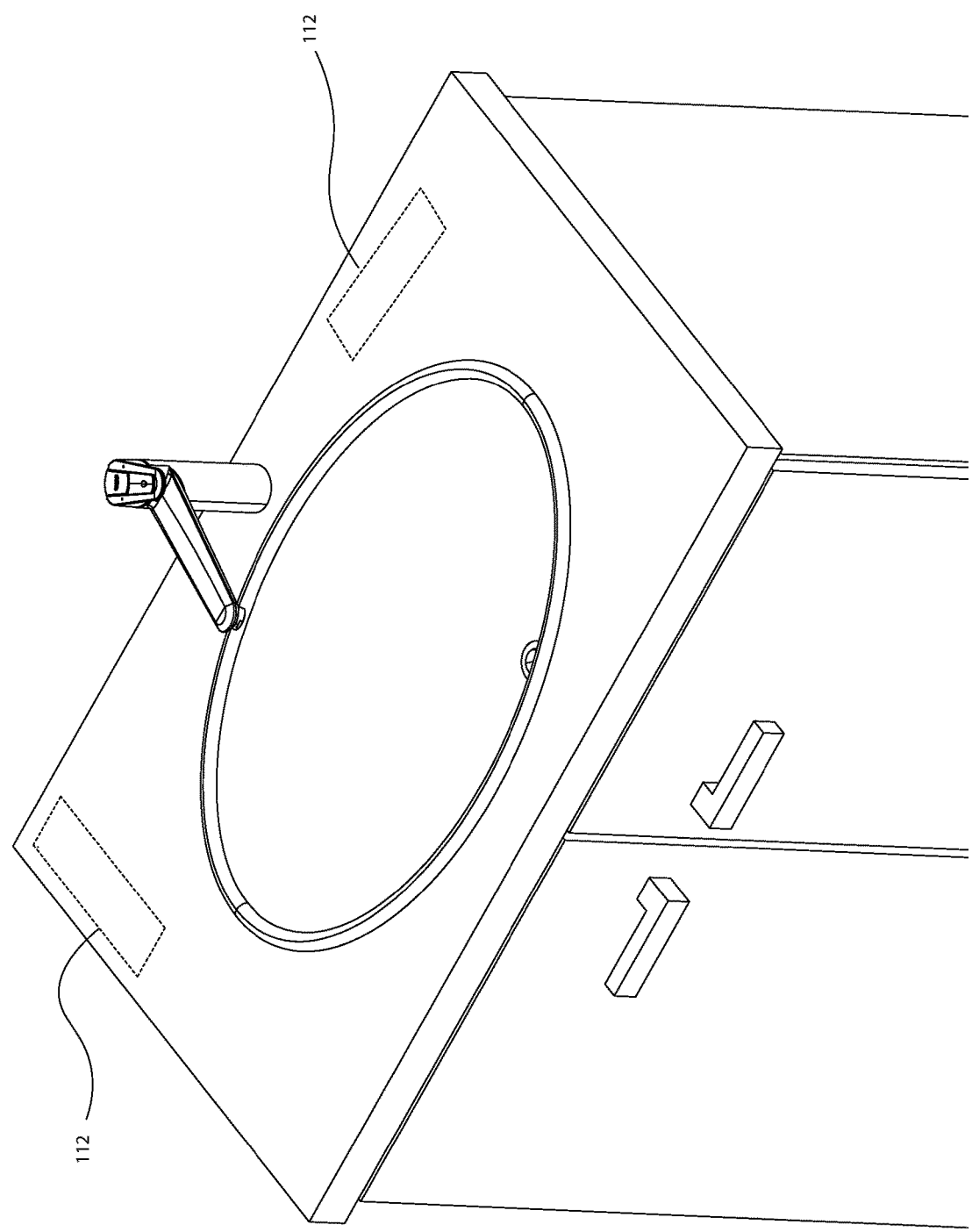
FIG. 1A show a sink with two possible footprints for embodiments of the invention.

FIG. 1A show a sink with two possible footprints for embodiments of the invention. This illustrates the limited real estate typical available around a sink and the importance of keeping footprints 112 small.

In some embodiments, the footprint is less than 15,000 mm$^2$. In other embodiments, the footprint is less than 10,000 mm$^2$. Generally, the width will be less than half of either the length or height dimension. This is particularly desirable for embodiments intended to be used in bathrooms in conjunction with hand washing. As a general matter the available space around a sink is relatively small and tend to be narrow. By keeping the footprint small, the disinfector can be deployed where it will be most useful, without interfering with normal sink operation.

Instead of standing on horizontal surface, some embodiments may include brackets 110 to facilitate mounting on a wall or other substantially vertical surface. Brackets 110 may be incorporated into the housing 102 or may be separately coupled thereto. Even in wall mounted embodiments, it is desirable to keep the width dimension small, so the disinfector remains relatively unobtrusive.

Figure 2:
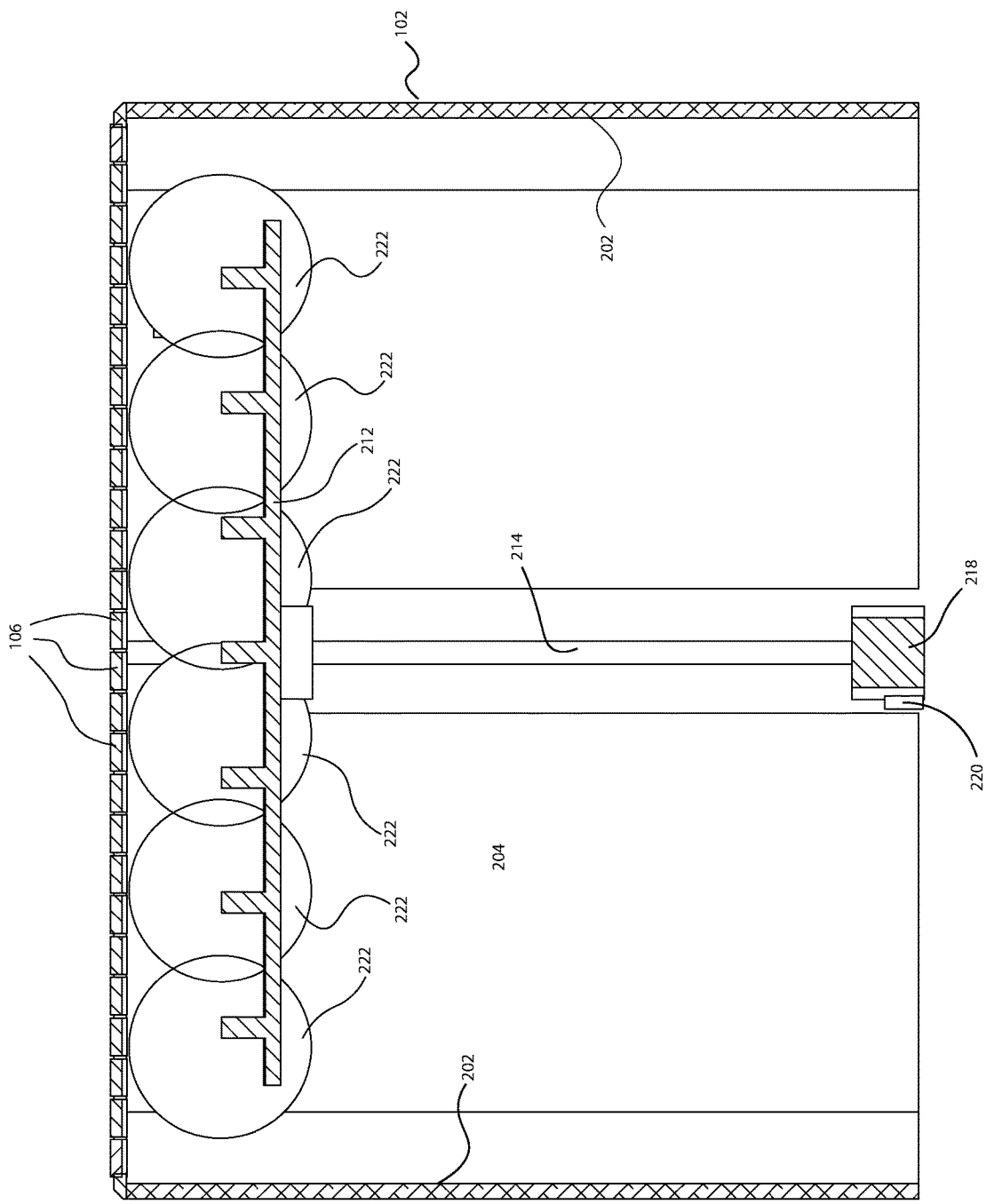
FIG. 2 is a section view of the embodiment of FIG. 1 taken through section A-A.

FIG. 2 is a section view of the embodiment of FIG. 1 taken through section A-A. Within the housing 102 is a carriage 212 attached to a drive 216. In use the carriage 212 receives the object 120. The drive 216 is driven by an actuator 218 to move the carriage (and therefor the object 120) though a UV-C light stripe 222 (shown schematically in this figure). Preferably, UV-C light having a wavelength in the range of 200-280 nm is used. More preferably, UV-C light falling in the range of 240-280 nm is used. As used herein "light" refers to UV-C light. Also as used herein, "light stripe" refers to an area of UV-C light having a length dimension greater than a width dimension.

Carriage 212 has a plurality of object retention features 214 adapted to receive the object of interest. In some embodiments, object retention features 214 may rely solely on gravity and/or friction to maintain objects thereon. In other embodiments the features may have a mechanical grip or clamp that holds the object of interest. In some embodiments, the features 214 are formed of quartz or fused silica glass as these materials do not attenuate UV-C light as does regular glass or polycarbonate. In one embodiment, ends of retention features terminate in a resilient clip with a jaw sized to accommodate a range of objects of interest. Generally, object retention features 214 will be formed from a substantially transparent synthetic material to permit UV light to pass through the material to reach the object of interest where the features 214 contact that object. In some embodiments, carriage 212 may be injection molded or extruded. As described further below, an upper surface of the carriage 212 may be made reflective to facilitate disinfection of the object of interest. Similarly, the underside 206 of fingers 106 are treated or coated to be reflective.

In various embodiments, actuator 218 could be a gyro, a servo, a stepper motor, a dc motor, a piezo electric motor, a solenoid or the like. The actuator 218 should be selected to provide sufficient torque to drive the drive 216 when loaded with an object 120. Drive 216 can be a screw drive, track drive, belt drive or any other transport that can cause relative movement between the carriage 212 and the light stripe 222. In some embodiment, the drive merely carries the object 120 into and out of the housing 102. In other embodiments, enable the selective exposure of the object 120 to the light stripes 222. A controller 220 selectively activates one or more emitters and the motor responsive to one or more sensors as described in more detail below. Controller 220 could be a microcontroller, microprocessor, application specific integrated circuit (APIC), field programmable gate array (FPGA) or the like.

In one embodiment, light stripe 222 is generated by an emitter configured to emit a stripe of sufficient length to be greater than the maximum side dimension of the object (e.g. object 120) to be exposed to the emitter. In one embodiment, the light stripe 222 emitted is greater than the length of the object access port 104. In one embodiment, the emitter is formed from a plurality of UV-C light emitting diodes LED's sufficient to create the light stripe 222 of the desired length by spacing the LED so that the cones of light produced overlap at a range of interest. For example, in one embodiment, six commercially available UV-C LEDs could be used spaced approximately 28.33 mm apart to yield a light stripe 222 approximately 194 mm long at a range of 16 mm (the stripe is longer than the internal cross dimension and is reflected by the side wall as described below). In another embodiment, a laser could be used to form the light stripe 222 by either spreading the laser beam or rastering the laser to form a stripe 222 of the desired length. Rastering can be performed by either moving the laser or moving a reflective element at which the laser is directed. In some embodiments, rastering the laser is under the control or controller 220.

In some embodiments, a second emitter creates a second light stripe that mirrors light stripe 222 and is emitted on an opposite side the object of interest. In this way, the full cross dimension of both sides of the object of interest will be covered by a light stripe. In some embodiment, more than one emitter may reside on a side of the object so that a single side of the object tis expose to more than one light stripe at the same time. At the limit, sufficient light stripes could be generated to cover an entire side of the object at one time.

In some embodiments, a transparent partition 204 may be interposed between the emitter(s) and the carriage 212. In principle, if the entire perimeter of the object is exposed to a light stripe, moving the object relative to the light stripe can expose the entire exposed surface area to the light stripe. The transparent partition 204 may be formed of quartz or fused silica glass to avoid blocking light from the emitters. The partitions reduce the risk of particulates entering the area of the housing 102 occupied by electronic components and prevent the possibility that the object of interest dislodges from the carriage 212 and interferes with the emitters or the transport mechanisms.

In some embodiments, interior surfaces such as end surfaces 202 of housing 102 are treated or coated to be reflective. In other embodiments, mirrored surfaces can be introduced beyond the limit of the internal volume expected to be occupied by the object of interest but still within the light stripe 222. In this way, light from the light stripe(s) 222 is reflected on to the ends of the object of interest. In other embodiments, additional emitters can be added to the ends to specifically direct light on the ends of the object 120.

Figure 3:
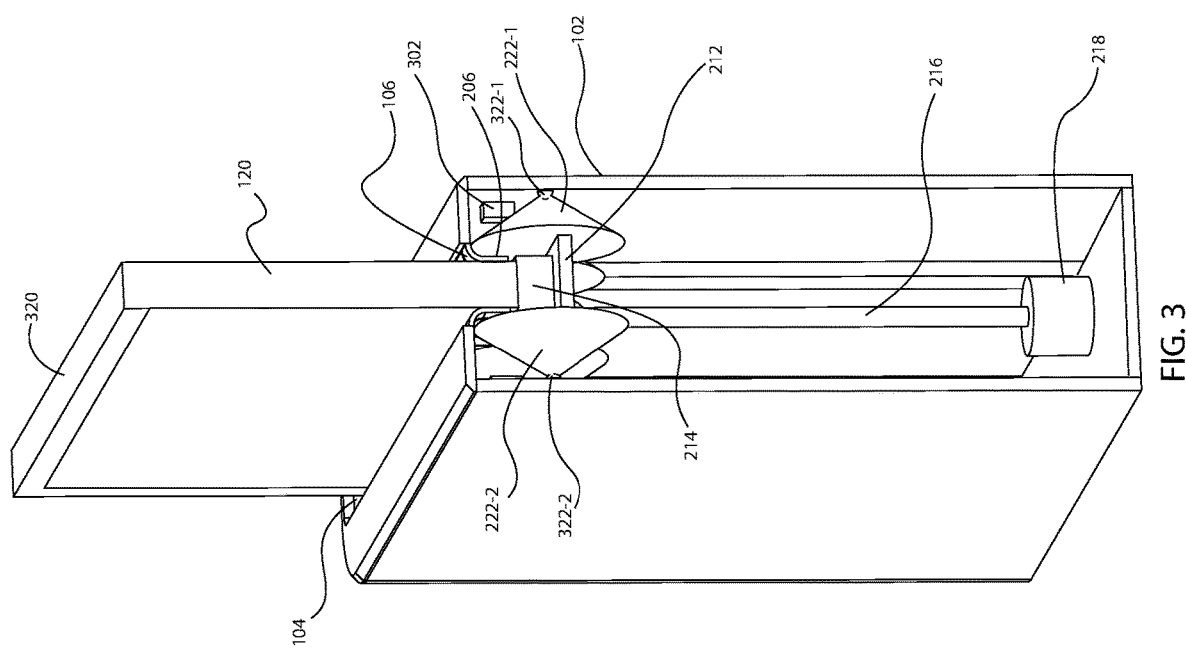
FIG. 3 is a perspective view of one embodiment of the invention with the end of the housing removed.

FIG. 3 is a perspective view of one embodiment of the invention with the end of the housing removed. In this view the object 120 has been inserted in the object access portal 104. The insertion causes the resilient fingers 106 to bend into the interior volume. In this position the underside 206 of the fingers 106 are exposed to the light strips 222-1 and 222-2 respectively (generically 222) for the right and left side fingers. Light stripes 222-1 and 222-2 are generated by emitters 322-1 and 322-2 respectively (generically 322).

In one embodiment, the emitters 322 include a plurality of UVC LEDs disposed along the inner walls of the long dimension of the housing 102. In one embodiment, the LEDs are positions so that the light stripes 222 at least slightly impinge upon the undersides 206 of the resilient fingers 106 and reflective end surfaces 202. In this way, substantially the entire extent of the underside 206 of the resilient fingers is disinfected as the object 120 enters the housing 102. Furthermore, the reflective undersides 206 reflect the light onto the upper edged of the object 120 once the object 120 is fully within the housing 102.

Object 120 can be inserted to rest upon object retention features 214 of carriage 212. One or more sensors 302 detect the insertion and signal the controller (not shown in this view) of the insertion. Responsive to the sensors, the controller activates the emitters 322 and manages the downward transport of the object by drive 216 that is driven by actuator 218 under controller's control. In addition to signaling the insertion of the object 120, the sensor(s) 302 signal when the trailing edge 320 of the object 120 passes the sensors such that the entire object 120 is within the housing 102. This lets the controller 220 know how far it must lower the object 120 to achieve intended disinfection. Sensor 302 may be any type of sensor that can detect the presence of the object 120. In one embodiment, an infrared (IR) break beam sensor may be used. In some embodiments, more than one IR break beam sensor may be used along the long dimension of the device. Using plural sensors can allow an embodiment to identify smaller object inserted and/or determine that the object 120 is fully/properly inserted before initiating the disinfection cycle. In some embodiments, a sensor may be located on the short sides (ends) of housing 102 the instead of or in addition to sensor 302 on the long side.

In one embodiment, the LED's of emitter 322-1, 3242-2 are rated for an energy emission of 12-15 mW. By appropriately driving the motor, the controller ensures that all parts of an exposed surface area of the object are exposed to sufficient UV-C energy to kill a desired pathogen or pathogens to an intended degree. In one embodiment, the "long" dimension of the of the object 120 is directly exposed to a light stripe 222 as the object 120 is moved into and subsequently out of the housing 102. The thin edge is exposed to reflected light. Light reflected off the reflective underside 206 of resilient fingers 106 exposes the top edge once the object 120 is fully within the housing 102. Light reflected off the carriage 212 exposes the bottom edge. Light reflected of the reflective interior end wall of housing 102 exposes the end edges.

Figure 4C:
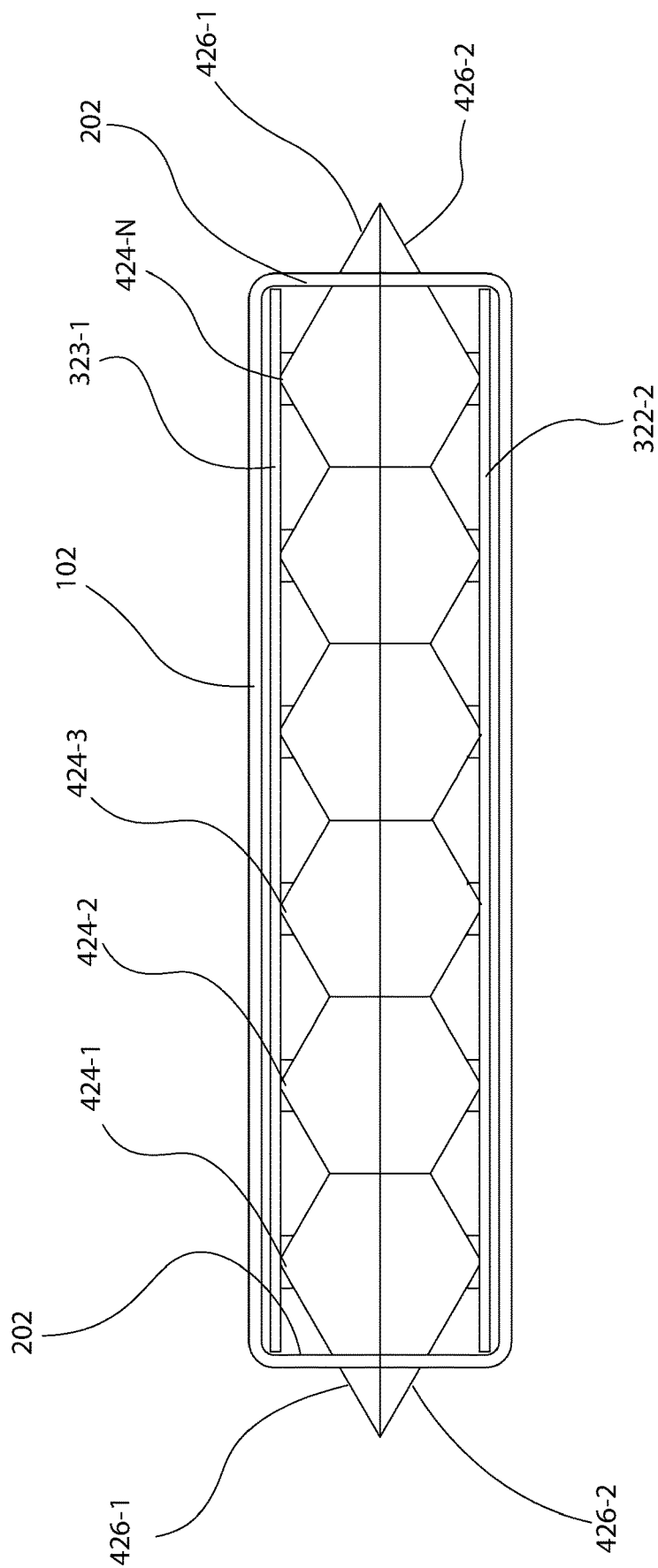

FIGS. 4A-4C illustrate edge disinfection schematically according to one embodiment of the invention. In one embodiment, when the object 120 is first inserted, sensor 302 signals the insertion causing the controller to activate the emitters 322. Emitters 322 generate light stripes 222 that project onto object 120. Carriage 212 receives the object 120 on its object retention features 214 such that the object 120 resides at or above the centerline of the light stripe 222-1, 222-2 and the reflective surface 512 of the carriage 212 resides below the center of the light stripes 222-1, 222-2. In this way, light is reflected from the reflective surface 512 (shown schematically as rays 524) to disinfect lower edge 420. After sufficient time has elapsed to complete the desired disinfection, the carriage 212 is lowered to transport the object through the light stripes 222.

Once the top edge 320 of the object 120 passes the sensor 302, the sensor signals the controller to allow the controller to know the range required to move the object 120 to complete the disinfecting process. As shown in FIG. 4B, to complete the process, the upper edge 320 is transported to be below the center of the stripes 222. Once the object is entirely within the housing 102, the resilient finger 106 resiliently recoil to occlude the object access port 104. This leaves reflective underside 206 to reflect the stripes 222 onto top side 320 (shown schematically as rays 432). The portion of the light stripes 222 that would extend through the object access portal 104 in the absence of fingers 106 is shown schematically as elements 422-1, 422-2, that corresponding light is instead reflected by reflective undersides 206. As noted above, underside 206 is exposed to disinfecting light while the object 120 is entering the housing 102. It also continues to be exposed to sterilizing light while the object 120 is fully within the housing 102. As a result, pathogens do not remain on the underside 206.

FIG. 4C schematically represent a top view of the emitters 224 that create the light stripes 222 that are reflected by end walls 202. In the shown embodiment, each emitter 224 is formed from a plurality of LEDs 424-1, 424-2, 424-3 424-N (generically 424). The number of LEDs 424 selected for a particular embodiment is driven by the desired length of stripe 222 and the desired overlap between light emitted by adjacent LEDs 424. In one embodiment, six LEDs 424 are used for each emitter. Other embodiments may use more or fewer LEDs 424. The ends 426-1, 426-2 (generically 426) of the stripes 222 shown schematically would extend as shown in the absence of end walls 202. End walls 202 are reflective and cause the ends 426 of the light stripes 222 to instead be reflected on the side edges of the object.

Studies reveal the virus that causes influenza is destroyed to a 90% effectiveness by exposure the of 3.4 $mJ/cm^2$ and 99% effectiveness with 10.2 $mJ/cm^2$ other pathogens are more or less susceptible to destruction by UV-C light. In some embodiments, it is desirable to have the process from insertion to removal be consistent with the time required for a user to e.g. wash their hands. Accordingly, some embodiments transport the object 120 at a rate where the process is completed in 90 seconds. In some embodiments, the expected light exposure is greater than 3 $mJ/cm^2$ in 90 seconds. In another embodiment, the exposure may be greater than 11 $mJ/cm^2$ in 90 seconds. In another embodiment, exposure may be greater than 30 $mJ/cm^2$ in 90 seconds. A smart phone sized 8.5 cm×16 cm×1.2 cm has a surface area of about 340.2 $cm^2$. Presuming twelve LEDs as describe above with a 12 mW rating, a surface area of 340.2 cm² can be exposed to greater than 11 mJ/cm² in under 30 seconds allowing a significant safety margin in a 90 second interval or even a 60 second interval. Some embodiments may use weaker emitters, fewer LEDs or for example have greater spacing between the emitters and the object, these variables can be addressed by driving the motor more slowly to insure longer exposure to the light stripe during the cycle. While maintaining cycle time under 90 seconds is believed to provide the greatest usability some embodiment may have a slower cycle time to but still provide touchless disinfection.

Figure 5:
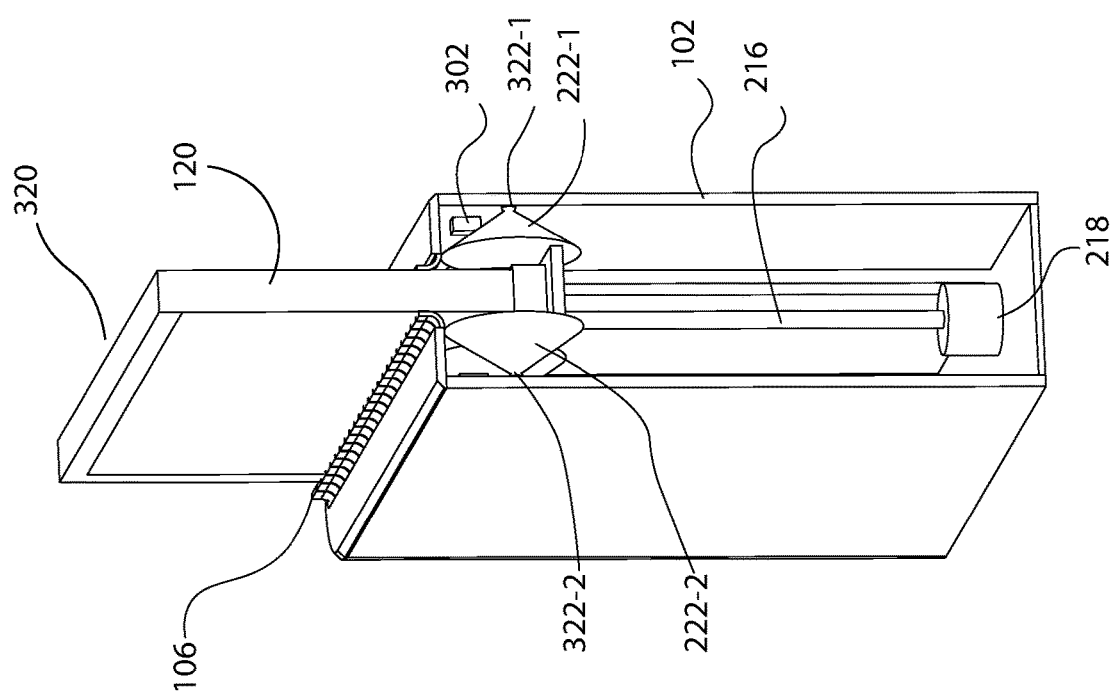
FIG. 5 is a perspective view of one embodiment of the invention with the end of the housing removed.

FIG. 5 is a perspective view of one embodiment of the invention with the end of the housing removed. FIG. 5 is identical to FIG. 3 above except it shows the object 120 leaving the housing 102 after the disinfecting process is complete. As drive 216 transports the object 120 up it passes through fingers 106 and is exposed for a user to remove it. Notably, on the underside of the fingers, which as described above, have been disinfected during the process come in contact with the disinfected object. As a result, pathogen between any surface in contact with the object 120 is avoided. Furthermore, since a user can insert and remove the phone without contact with the disinfecting apparatus, a touchless disinfection process is achieved. Sensor 302 detects when the object 120 is removed and can signal the controller to turn off the emitters 224.

Some embodiments, descend and return at a substantially constant rate with disinfection occurring both while the object is transitioning downward and while it is transition upwards. Other embodiment may perform the entire disinfection while the object moves in one direction and move the object in the other direction at a greater rate of speed.

Figure 6:
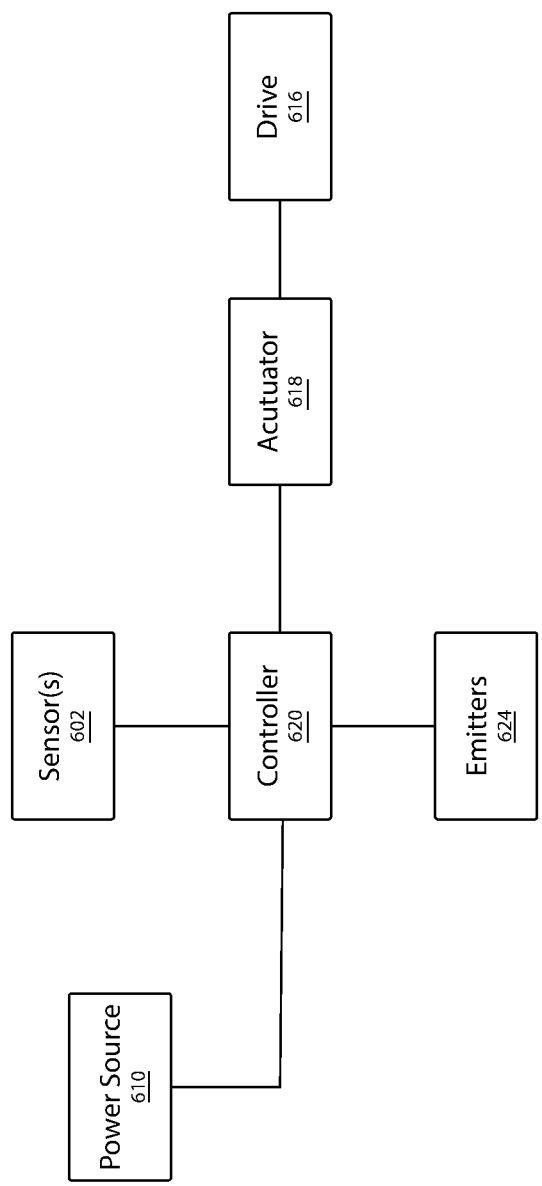
FIG. 6 is a block diagram of active components of a system of one embodiment of the invention.

FIG. 6 is a block diagram of active components of a system of one embodiment of the invention. Controller 620 is coupled to a power source 610 that supplies power to the system. In one embodiment, power source 610 is portable such as a lithium ion battery or the like. In other embodiments, the power source could be a wall outlet or other fixed source of electrical power. Sensors 602 signal the processor responsive to an event to indicate that a disinfection process should begin. Sensors 602 could be an IR beam break sensor, a pressure sensor, or any other sensor that can adequately detect the presence of an object to be disinfected. In some embodiments, the controller 620 may poll the sensors 602. In other embodiments, the sensors 602 may sent asynchronous events such as interrupts to the controller 620. Controller 620 is coupled to one or more emitters 624. Responsive to an event indicating the beginning of a disinfection session, the controller 620 turns on the emitters 624 to project one or more light stripes into a disinfection zone. The controller 620 is couple to the actuator 618 which is couple to a drive 616. Under the control of the controller 620, the actuator 618 causes the drive 616 to cause relative motion between the emitters and the object. That is, in some embodiment, the emitters may be moved while the object is held still and in other embodiments, the emitters may remain still while the object is moved. In still other embodiments, both the emitters and the object may be moved.

Figure 7A:
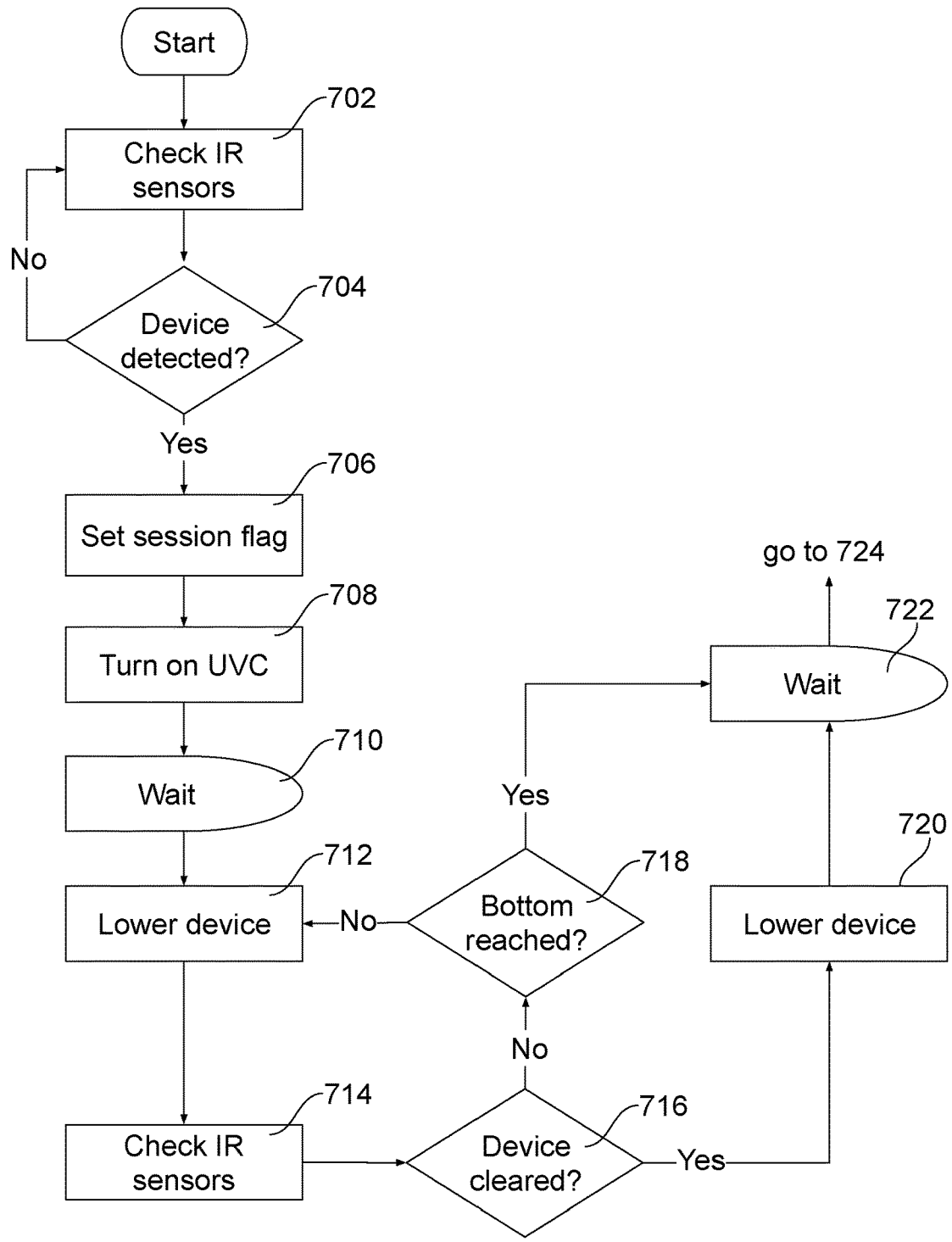
FIGS. 7A and 7B are a flow diagram of operation according to one embodiment of the invention.
Figure 7B:
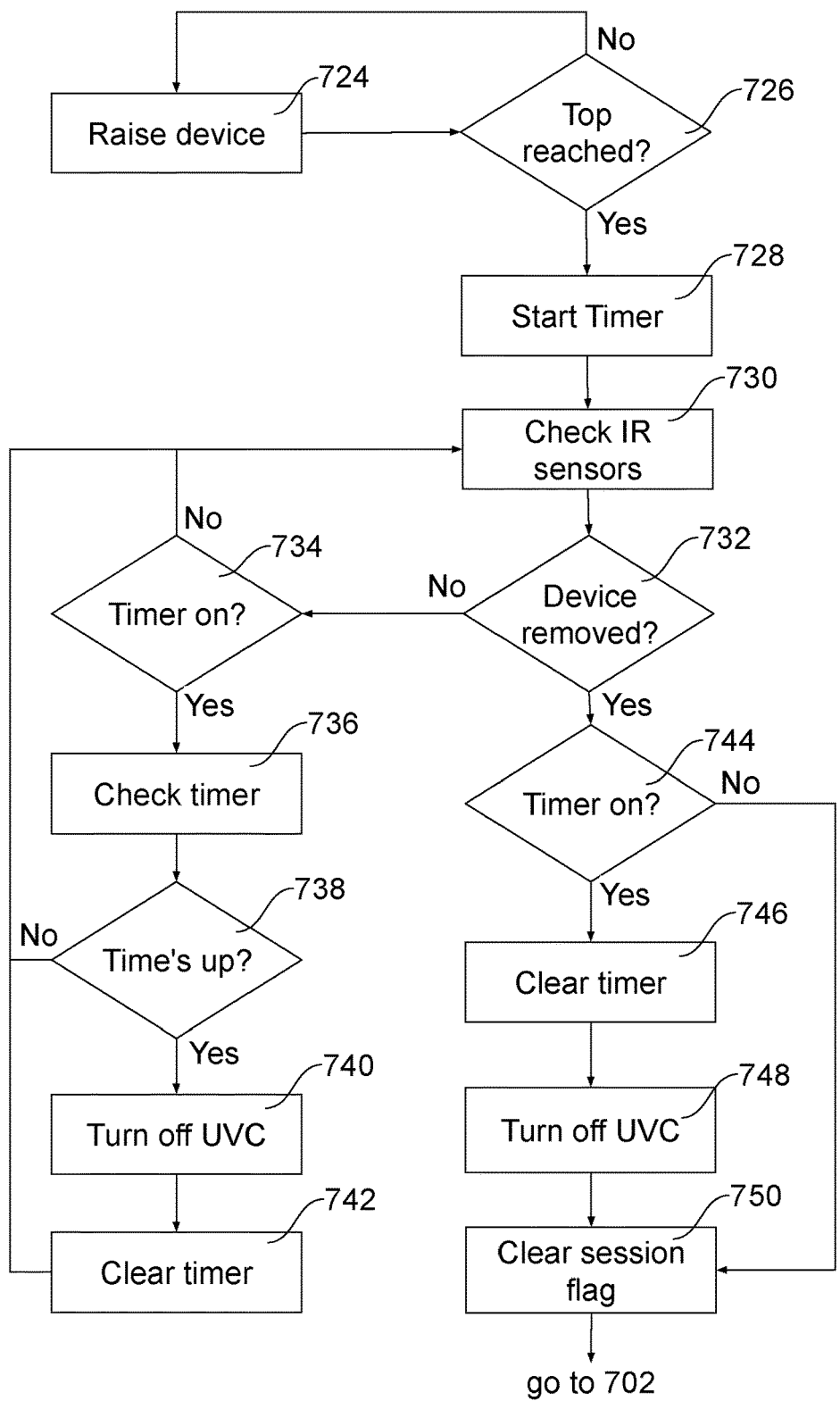

FIG. 7 is a flow diagram of operation according to one embodiment of the invention. At block 702, the controller checks the sensors. At decision block 704, the controller interprets the sensor readings to determine if an object is present to be disinfected. In not the sensors are periodically checked until an object is identified. If an object is identified, the controller sets a session flag at block 706. The presence of the session flag prevents misinterpretation of subsequent sensor readings. At block 708, the controller turns on the emitters to generate one or more UV-C light stripes.

At block 710, the controller waits a predetermined time. This wait state is timed to ensure adequate exposure of the bottom edge of the object from the light reflected off the carriage. In some embodiments, the 5-6 seconds has been found to be an adequate wait. Other embodiments may have a longer or shorter wait state. At block 712, the controller causes the actuator to lower the object into the housing. The sensors are checked at block 714. Then a determination is made at decision block 716 whether the object has cleared the sensors. If the session flag is set and the sensors no longer detect the object, the object is deemed to have cleared the sensors and be fully within the housing. If that is not the case a determination is made if the bottom of the drive has been reached at decision block 718. If not, the controller continues cause the object to be lowered and the loop repeats. In some embodiment, the lowering may be substantially continuous, in other embodiments, the lowering is step wise at some faction such as ½ or ¾ of the stripe width.

If the object has cleared the sensor, at block 716, the object is lowered further at block 720. In some embodiments, the object is lowered until its upper edge is below the midway point of the light stripe. The additional lowering required can be determined by the controller based on the point the sensors no longer detected the object. Of course, the amount of lowering possible is constrained by the bottom of the drive. Once the bottom is reached or the object has been lowered to a desired lowest position, the controller again waits at block 722 to allow adequate light to disinfect the top edge. In some embodiments, the 5-6 seconds has been found again to be an adequate wait. Other embodiments may have a longer or shorter wait state.

Thereafter at block 724, the controller causes the actuator to raise the object. At decision block 726, a determination made if the carriage has reached the top. If is has not the raising continues until the top is reached. If the top is reached, a timer is started at block 728. The timer is used to force a shut off of the emitters if the object is not removed. Accordingly, at block 730 the sensors are checked. At decision block 732, a determination is made if the object has been removed based on the sensor reading. If it has not, a determination is made at decision block 734 whether the timer is on. If the timer is on, the timer is checked at block 736. A determination is then made at decision block 738 whether the timer has timed out. If it has the emitters are turned off at block 740 and the timer is cleared at block 742. If the timer is not on at block 734, the time is not up at block 738, or after clearing the timer, the controller again checks the sensors and cycles until the object is removed.

If at decision block 732 the device is determined to have been removed, a determination is made at decision block 744 whether the timer is still on. If the timer is still on it is cleared at block 746 and the emitters are turned off at block 748. After turning off the emitters, or if the timer was no longer on at block 744, the session flag is cleared at block 750. Thereafter the system progresses to block 702 and cycles until a new object is introduced.

Embodiments described above hold the emitters still and the object is moved by a linear drive past the emitter. It is contemplated that that some embodiments may for example have a cylindrical housing with a rotational drive such as a turn table. The turntable could be raised and lowered to accept and eject the object of interest. An emitter on the cylinder wall could cast a light stripe on the object that is rotated by the turn table. Rotation could be controlled to adjust exposure time based on the distance of the emitter from the object as it rotates. The object may be elevated off the turntable by object UV transmissive object retention features and the surface of the turntable may be reflective. In another embodiment, the emitter could be driven to circumnavigate a cylindrical space containing the object and a platform could be provided to lower the object into position for disinfection and raise the object for removal.

It should be understood that directional references in this application are intended for convenience of description only. For example, instead of a vertical orientation, embodiment of the invention may accept an object through an access port in a side wall and transport the object horizontally past a vertically oriented emitter. Embodiments in arbitrary orientations are contemplated. Emitters collectively should cover the perimeter of the object at some time during the transport cycle.

Some aspects of various aspect of embodiments of the invention are described with reference to a flow diagram, it should be understood that in some embodiments elements of the flow diagrams may be performed in a different order or in parallel to rather than the order shown. Applicant expressly does not intend to imply a particular temporal relationship unless expressly stated in the claims that follow. Furthermore, to the extent that a decision element is included in the flow diagram, in some cases, that decision may be implicit or default. That is asynchronous selection of an execution path, e.g., interrupt driven, is within the scope and contemplation off embodiments of the invention.

In the foregoing specification, the invention has been described with reference to specific embodiments thereof. It will, however, be evident that various modifications and changes can be made thereto without departing from the broader spirit and scope of the invention as set forth in the appended claims. The specification and drawings are, accordingly, to be regarded in an illustrative rather than a restrictive sense.

What is claimed is:

1. An apparatus comprising:
a housing defining an internal volume including a disinfection zone and an object entry port of a size to permit entry by an object of interest, the object of interest having an exposed surface area;
a first emitter to emit a stripe of light with a wavelength in the range of 200-280 nm from a first side of the disinfection zone at a first distance from the disinfection zone;
a drive to cause relative movement between the first emitter and the object of interest;
a carriage to hold the object of interest during disinfection; and
a controller to control the relative movement based on the first distance and responsive to a characteristic of the object of interest; and
wherein, in use, the exposed surface area is subjected to greater than 3 mJ/cm$^2$ of light of the wavelength in less than 90 seconds and wherein the object of interest is introduced directly into the object entry port without external packaging, and
wherein, contact between the carriage and the object of interest is less than 6% of the exposed surface area of the object of interest.

2. The apparatus of claim 1 wherein the transport comprises:
a linear drive; and
a platform to retain the object of interest, the platform moved past the first emitter by the linear drive.

3. The apparatus of claim 1 wherein the first emitter comprises:
a plurality of light emitting diodes spaced such that emitted light from adjacent members of the plurality overlaps.

4. The apparatus of claim 1 wherein the emitter comprises:
a laser and wherein the laser is one of rastered or spread to form the stripe.

5. The apparatus of claim 1 further comprising:
a resilient closure allowing the object to pass through the port while occluding light from within the volume, the resilient closure having an internally exposed side and an externally exposed side, wherein the resilient closure contacts a first side and second and is configured to at least partially support the object as it enters the housing.

6. The apparatus of claim 1 further comprising:
a second emitter to emit a second stripe of light with a wavelength in the range of 200-280 nm from a second side of the disinfection zone at a second distance from the disinfection zone, the second side opposed to the first side.

7. The apparatus of claim 1 further comprising:
a sensor operatively coupled to the controller to signal the presence of the object in the port wherein the controller activates the transport responsive to the presence of the object.

8. The apparatus of claim 7 wherein the sensor further signals to the controller when the object is fully within the internal volume and wherein the controller determines a range of transport responsive to the signals.

9. A touchless disinfection apparatus comprising:
a housing defining an internal volume including a disinfection zone and an object entry port of a size to permit entry by an object of interest, the object of interest having an exposed surface area;
a first emitter to emit a stripe of light with a wavelength in the range of 200-280 nm from a first side of the disinfection zone at a first distance from the disinfection zone;
a drive to transport the object into the disinfection zone and exposes the object out of the housing after disinfection;
a carriage to hold the object of interest during disinfection; and
a controller to power the first emitter and activate the drive;
wherein, in use, the object of interest is introduced directly into the object entry port without external packaging, and
wherein, contact between the carriage and the object of interest is less than 6% of the exposed surface area of the object of interest.

10. The apparatus of claim 9 wherein the drive causes relative movement between the first emitter and the object of interest based on at least one characteristic of the object of interest.

11. The apparatus of claim 9 further comprising:
a bracket coupled to the housing to couple the housing to a substantially vertical surface.

12. The apparatus of claim 9 wherein the housing has a gross geometry and wherein the gross geometry does not change while the object is moved into and out of the housing.

13. An apparatus comprising:
a housing defining an internal volume including a disinfection zone and an object access port of a size to permit entry by an object of interest;
means for emitting light with a wavelength in the range of 200-280 nm sufficient to cover a perimeter of the object within the disinfection zone;
means for transporting the object into the housing and exposing the object out of the housing after disinfection is complete; and
means for controlling the means for transporting and the means for emitting to provide greater than 3 mJ/cm$^2$ of light of the wavelength in less than 90 seconds to an exposed surface area of the object of interest,
wherein, in use, the object of interest is introduced directly into the object entry port without external packaging, and
wherein, contact between the means for transporting and the object less than 6% of the exposed surface area of the object of interest.

14. The apparatus of claim 13 further comprising:
means for resiliently occluding the object access port while allowing the object to pass through the port while occluding light from within the volume, the means having an internally exposed side and an externally exposed side and wherein the internally exposed side is reflective.

15. The apparatus of claim 13 further comprising:
means for sensing operatively coupled to the means for controlling to signal the presence of the object in the port wherein the means for controlling activates the means for transporting responsive to the presence of the object.

16. The apparatus of claim 13 wherein the means for sensing further signals to the means for controlling when the object is fully within the internal volume and wherein the means for controlling determines a range of transport responsive to the signals.

17. The apparatus of claim 13 wherein the exposed surface area is exposed to greater than 30.0 mJ/cm2 of light of the wavelength in less than 90 seconds.

18. The apparatus of claim 13 further comprising:
means for causing relative motion between the object of interest and the means for emitting.

19. The apparatus of claim 13 where the housing has a gross geometry including a length, a width and a height and wherein the gross geometry remains substantially unchanged throughout operation.

* * * * *